United States Patent
Morrison et al.

(10) Patent No.: US 8,247,593 B2
(45) Date of Patent: Aug. 21, 2012

(54) PROCESS FOR PREPARING SUBSTITUTED 7-CYANO QUINONE METHIDES

(75) Inventors: Christopher F. Morrison, Richmond, TX (US); Joseph Paul Street, Friendswood, TX (US)

(73) Assignee: Nalco Company, Naperville, IL (US)

( * ) Notice: Subject to any disclaimer, the term of this patent is extended or adjusted under 35 U.S.C. 154(b) by 721 days.

(21) Appl. No.: 12/119,930

(22) Filed: May 13, 2008

(65) Prior Publication Data
US 2009/0287013 A1    Nov. 19, 2009

(51) Int. Cl.
*C07C 253/14* (2006.01)
(52) U.S. Cl. .................................... 558/342
(58) Field of Classification Search .............. 558/342
See application file for complete search history.

(56) References Cited

U.S. PATENT DOCUMENTS

| | | | |
|---|---|---|---|
| 2,459,597 A | | 1/1949 | Stillson et al. |
| 3,257,321 A | * | 6/1966 | Odenweller ............... 508/587 |
| 4,032,547 A | * | 6/1977 | Bacha et al. ............... 552/304 |
| 5,583,247 A | | 12/1996 | Nesvadba et al. |
| 5,616,774 A | | 4/1997 | Evans et al. |
| 5,750,765 A | | 5/1998 | Nesvadba et al. |
| 7,045,647 B2 | | 5/2006 | Benage |

OTHER PUBLICATIONS

Nesvadba "Easy Large Scale Syntheses of 2,6-Di-t-butyl-7-cyano-, 7-carboxy-, and 7-methoxycarbonyl Quinone Methides" Synthetic Communications, 2000, vol. 30, No. 15, pp. 2825-2832.*
Dozeman et al. "Chemical Development of a Pilot Scale Process for the ACAT Inhibitor 2,6-Diisopropylphenyl [(2,4,6-Triisopropylphenyl)acetyl]sulfamate" Organic Process Research & Development, 1997, vol. 1, pp. 137-148.*
McMurry, John "Organic Chemistry—Fourth Edition" Brooks/Cole Publishing Company, 1996, pp. 382-383.*
Chemical Development of a Pilot Scale Process for the ACAT Inhibito 2,6-Diisoprpylphenyl [(2,4,6-Tritsopropylphenyl)acetyl]sulfamate by Gary J. Dozeman et al. *Org. Process Res. Dev.*, 1997, 1 (2), 137-148.

* cited by examiner

*Primary Examiner* — Joseph Kosack
(74) *Attorney, Agent, or Firm* — Benjamin E. Carlsen; Andrew D. Sorenson

(57) ABSTRACT

A one-pot process of preparing a substituted 7-cyano quinone methide in which i) a substituted phenol is chloromethylated to form a substituted 4-chloromethylphenol; ii) converting the substituted 4-chloromethylphenol to a substituted 4-cyanomethylphenol; and iii) oxidizing the substituted 4-cyanomethylphenol to the substituted 7-cyano quinone methide, where steps i)-iii) are carried out in a single reaction vessel in a solvent system comprising water and one or more organic solvents and where after steps i) and ii) the aqueous portion of the reaction mixture is removed and the reagents for the subsequent step are added in aqueous solution. The 7-cyano quinone methides are effective inhibitors of the polymerization of reactive monomers.

13 Claims, No Drawings

PROCESS FOR PREPARING SUBSTITUTED 7-CYANO QUINONE METHIDES

TECHNICAL FIELD

This invention relates to a process for preparing substituted 7-cyano quinone methides from substituted 4-cyanomethylphenols using a coupled oxidation system comprising an iron cyanide compound and a persulfate and to a one-pot synthesis of substituted 7-cyano quinone methides from substituted phenols. The substituted 7-cyano quinone methides are useful for inhibiting the polymerization of reactive monomers.

BACKGROUND OF THE INVENTION

Quinone methides substituted at the 7 position are known to inhibit the polymerization of reactive monomers such as styrene. See U.S. Pat. Nos. 5,583,247, 5,750,765 and 7,045,647. More particularly, substituted 7-cyano quinone methides of formula (1) in comparison to the current commercial inhibitor 2,4-dinitro-sec-butylphenol (DNBP) are less toxic, can reduce potential NOx emissions by up to 90% and have improved performance. There is not, however, a practical process for manufacturing substituted 7-cyano quinone methides.

SUMMARY OF THE INVENTION

In an embodiment, this invention is a process of preparing a substituted 7-cyano quinone methide of formula (1)

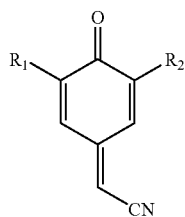

(1)

wherein $R_1$ and $R_2$ are independently selected from $C_4$-$C_{18}$ alkyl, $C_5$-$C_{12}$ cycloalkyl, phenyl and $C_7$-$C_{15}$ phenylalkyl comprising i) reacting a substituted phenol of formula (2)

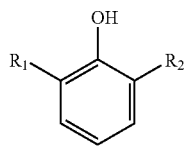

(2)

with paraformaldehyde and aqueous hydrochloric acid to form a substituted 4-chloromethylphenol of formula (3);

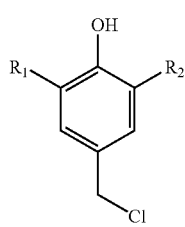

(3)

ii) reacting the substituted 4-chloromethylphenol of formula (3) with a cyanide salt in the presence of a catalyst to form a substituted 4-cyanomethylphenol of formula (4);

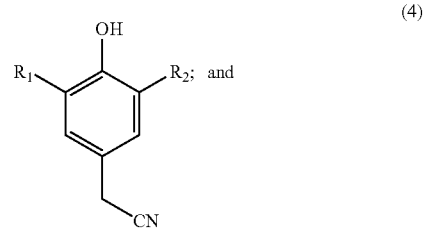

(4)

iii) reacting the substituted 4-cyanomethylphenol of formula (4) with a water-soluble iron cyanide salt, a water-soluble persulfate salt and base to form the substituted 7-cyano quinone methide, wherein steps i)-iii) are carried out in a single reaction vessel in a solvent system comprising water and one or more organic solvents and wherein after each of steps i) and ii) the aqueous portion of the reaction mixture is removed and the reagents for the subsequent step are added to the reaction vessel in aqueous solution or water and the reagents are added to the reaction vessel separately.

DETAILED DESCRIPTION OF THE INVENTION

As used herein, "alkoxy" means an alkyl group, as defined herein, attached to the parent molecular moiety through an oxygen atom. Representative alkoxy groups include methoxy, ethoxy, propoxy, butoxy, and the like.

"Alkyl" means a monovalent group derived from a straight or branched chain saturated hydrocarbon by the removal of a single hydrogen atom. Representative alkyl groups include methyl, ethyl, n- and iso-propyl, n-, sec-, iso- and tert-butyl, n-octyl, and the like.

"Cycloalkyl" means a monovalent group derived from a monocyclic or bicyclic saturated carbocyclic ring compound by the removal of a single hydrogen atom. Representative cycloalkyl include cyclopropyl, cyclobutyl, cyclopentyl, cyclohexyl, bicyclo[2.2.1]heptanyl, bicyclo[2.2.2]octanyl, and the like.

"Haloalkyl" means an alkyl group, as defined herein, having one, two, or three halogen atoms attached thereto and is exemplified by such groups as chloromethyl, bromoethyl, trifluoromethyl, and the like.

"Halogen" means Cl, Br, F or I.

"Phenyl" means an aromatic, carbocyclic group of formula $C_6H_5$ where one or more of the H atoms may be replaced with a $C_1$-$C_4$ alkyl, $C_1$-$C_4$ alkoxy, halogen or $C_1$-$C_4$ haloalkyl group.

"Phenylalkyl" means a phenyl group as defined herein, attached to the parent molecular moiety through an alkylene group. Representative phenylalkyl groups include phenylmethyl, phenylethyl, phenylpropyl, and the like.

In an embodiment, this invention is a one-pot synthesis of a substituted 7-cyano quinone methide of formula (1) which comprises converting substituted phenol (2) to substituted 4-chlormethylphenol (3), converting substituted 4-chlormethylphenol (3) to substituted 4-cyanomethylphenol (4); and oxidizing substituted 4-cyanomethylphenol (2) to substituted 7-cyano quinone methide (1). Each reaction is conducted in a mixture of water and organic solvents and after each conversion the aqueous portion of the reaction mixture is drawn off and the organic product solution is used as-is in the subsequent transformation without isolation of the intermediate products.

In a representative procedure, the substituted phenol (2) is melted or added as a solution in an organic solvent to a mixture of paraformaldehyde and aqueous hydrochloric acid under inert atmosphere and the mixture is heated and stirred at the reaction temperature for about 4-16 hours. The reaction mixture is then diluted with an organic solvent and aqueous phase is removed from the reaction vessel to provide a solution of the substituted 4-chloromethylphenol (3) in the organic solvent. The organic solution of the substituted 4-chloromethylphenol (3) may be used as is in the subsequent conversion or in an alternative embodiment any water remaining in the organic solution may be removed by azeotropic distillation.

Representative organic solvents include pentane, heptane, hexane, benzene, ethylbenzene, toluene, and the like and mixtures thereof. In an embodiment, the solvent is toluene, ethylbenzene or a mixture thereof.

The preparation of substituted phenols is described in U.S. Pat. No. 2,459,597. Substituted phenols are also commercially available, for example from SIGroup International, Schenectady, N.Y., and Aldrich, Milwaukee, Wis.

In an embodiment, the substituted phenol (2) is reacted with about 1 to about 5 molar equivalents of paraformaldehyde and about 2 to about 5 molar equivalents of concentrated aqueous hydrochloric acid at a temperature of about 55 to about 115° C. In an embodiment, the substituted phenol (2) is reacted with about 2 to about 3 molar equivalents of paraformaldehyde and about 3 to about 4 molar equivalents of concentrated aqueous hydrochloric acid.

The substituted 4-chloromethyl phenol (3) is then reacted with a cyanide salt in the presence of a tetralkylammonium halide catalyst at a temperature of about 55 to about 90° C. to form the substituted 4-cyanomethyl phenol (4).

In a typical procedure, an aqueous solution of cyanide salt and tetralkylammonium halide is added to the solution of the substituted 4-chloromethylphenol (3) in an organic solvent prepared as described above. Additional water and/or organic solvent may be added to the reaction mixture as necessary. The reaction mixture may be heated to obtain a suitable reaction rate. In an embodiment, the reaction is conducted at about 75-80° C. After conversion of the substituted 4-chloromethylphenol (3) to the substituted 4-cyanomethylphenol (4), the aqueous phase is drawn off and the organic solution of substituted 4-cyanomethyl phenol (4) is used as is in the next step.

In an embodiment, the substituted 4-chloromethylphenol (3) is reacted with about 1 to about 3 molar equivalents of a salt of formula MCN where M is K or Na and about 1 to about 5 mole percent of a tetralkylammonium halide catalyst of formula $R_4N^+X^-$ where R is $C_1$-$C_4$ alkyl and X is Cl or Br.

In an embodiment, the substituted 4-chloromethylphenol (3) is reacted with about 1 molar equivalent of sodium cyanide and about 1 mole percent of tetrabutylammonium bromide to form the substituted 4-cyanomethylphenol (4).

The substituted 4-cyanomethylphenol (4) is then converted to the substituted 7-cyanoquinone methide of formula (1) using a coupled oxidation system comprising an iron cyanide compound selected from an oxidant comprising a ferricyanide or a reductant comprising a ferrocyanide and a persulfate. In this coupled oxidation system, ferrocyanide is oxidized to ferricyanide by the persulfate, and ferricyanide is subsequently reduced to ferrocyanide by the substituted 4-cyanomethylphenol. These oxidation-reduction reactions continue until all the 4-cyanomethylphenol is oxidized to 7-cyanoquinone methide. Since ferrocyanide is regenerated to ferricyanide, either can be used in the initial reaction mixture.

Representative ferricyanides and ferrocyanides include sodium, ammonium, potassium, calcium, barium, magnesium, and lithium ferricyanides and ferrocyanides. In an embodiment, the ferricyanide and ferrcyanide have formula $K_xFe(CN)_6$ wherein x is 3 or 4. In an embodiment, the iron cyanide salt is potassium hexacyanoferrate.

The ferrocyanides are oxidized to ferricyanides by certain water-soluble persulfate salts. Representative persulfate salts include sodium, ammonium, potassium, calcium, barium, magnesium and lithium persulfate, and the like. In an embodiment, the persulfate is sodium persulfate or potassium persulfate.

The amount of iron cyanide salt and water-soluble persulfate salt used depends on the amount of phenol present and other variables such as mixing time, temperature, pressure and the like and can be determined empirically by one of skill in the art. In an embodiment, about 0.1 to 1 molar equivalents of a water-soluble iron cyanide salt and about 0.1 to about 1 molar equivalents of a water-soluble persulfate salt relative to phenol is used. In an embodiment, about 0.25 molar equivalents of water-soluble iron cyanide salt and about 1.0 molar equivalents of water-soluble persulfate salt is used.

The oxidation-reduction reaction normally takes place in aqueous solution at a pH above 7. In order to maintain the pH above 7 a base may be added to the reaction. Suitable bases include any non-interfering compound which can alter and/or maintain the solution pH within the desired range. For example, the phosphates, carbonates, bicarbonates or hydroxides which buffer within the pH range of 7 to 12 are useful. Representative bases include sodium hydroxide, potassium hydroxide, sodium carbonate, and the like. The base is used at levels sufficient to keep the solution pH above 7. In an embodiment, about 1 to about 3 molar equivalents of base, relative to phenol, is used. In an embodiment, the base is potassium hydroxide.

The oxidation of 4-cyanomethylphenol to 7-cyanoquinone methide may be accomplished by mixing the solution of 4-cyanomethylphenol in an organic solvent described above with an aqueous solution of iron cyanide salt, persulfate salt and base at ambient temperature. The 4-cyanomethylphenol, base, iron cyanide salt and persulfate salt can be added to the reaction mixture in any order, however it is generally preferred that the persulfate salt is added last.

In a typical procedure, water is added to the organic solution of substituted 4-cyanomethylphenol (4) in about a 1:1 ratio by volume. To this mixture is sequentially added base, iron cyanide salt and persulfate salt. The persulfate salt may be added in portions. The mixture is then stirred at ambient temperature for a period sufficient to oxidize the 4-cyanomethylphenol to the 7-cyanoquinone methide. The aqueous phase is then drawn off to provide the 7-cyanoquinone methide (1) as a solution in the organic solvent which can be used as-is or dried and concentrated.

In an embodiment, the substituted 4-cyanomethylphenol is reacted with about 0.1 to 1 equivalents of the water-soluble iron cyanide salt, about 0.1 to 1.0 equivalents of a water-soluble persulfate salt and about 1 to 3 equivalents of base.

In an embodiment, the substituted 4-cyanomethylphenol is reacted with less than 0.25 equivalents of potassium hexacyanoferrate, 1.0 equivalents of potassium persulfate and 2.2 equivalents of KOH. In an embodiment, the reaction is conducted in 1:1 water:ethylbenzene.

In alternative embodiments, the organic solution of substituted 4-chloromethyl phenol (2) and substituted 4-cyanomethyl phenol (3) may be removed and the intermediates purified prior to the subsequent reactions. For example, the substituted 4-cyanomethylphenol (4) may be isolated by filtration from the cooled reaction mixture.

The substituted 7-cyano quinone methides prepared as described herein are useful for preventing the polymerization of reactive monomers including vinyl aromatic monomers such as styrene, α-methylstyrene, vinyltoluene and divinylbenzene, acrylic monomers such as (meth)acrylic acid, and its esters and amides, unsaturated asters such as vinyl acetate and unsaturated polyesters having a tendency to polymerize at elevated temperatures.

Representative substituted 7-cyano quinone methide polymerization inhibitors prepared according to this invention include (3,5-di-tert-butyl-4-oxocyclohexa-2,5-dienylidene) acetonitrile; (3,5-di-tert-amyl-4-oxocyclohexa-2,5-dienylidene)acetonitrile; (3,5-di-n-dodecyl-4-oxocyclohexa-2,5-dienylidene)acetonitrile; (3,5-di-cyclopenyl-4-oxocyclohexa-2,5-dienylidene)acetonitrile; (3,5-di-cyclohexyl-4-oxocyclohexa-2,5-dienylidene)acetonitrile; (3,5-di-phenyl-4-oxocyclohexa-2,5-dienylidene)acetonitrile; and the like.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A process of preparing a substituted 7-cyano quinone methide of formula

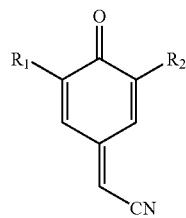

wherein $R_1$ and $R_2$ are independently selected from $C_4$-$C_{18}$ alkyl, $C_5$-$C_{12}$ cycloalkyl, phenyl and $C_7$-$C_{15}$ phenylalkyl comprising i) reacting a substituted phenol of formula

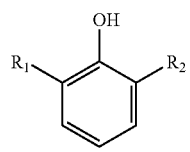

with paraformaldehyde and aqueous hydrochloric acid to form a substituted 4-chloromethylphenol of formula;

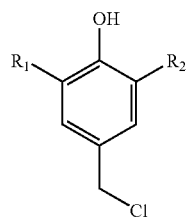

ii) reacting the substituted 4-chloromethylphenol prepared in step i) with a cyanide salt in the presence of a catalyst to form a substituted 4-cyanomethylphenol of formula

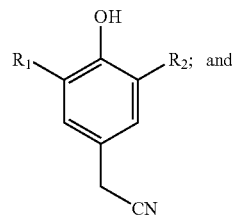

iii) reacting the substituted 4-cyanomethylphenol prepared in step ii) with a water-soluble iron cyanide salt, a water-soluble persulfate salt and base to form the substituted 7-cyano quinone methide, wherein steps i)-iii) are carried out in a single reaction vessel in a solvent system comprising water and one or more organic solvents and wherein after steps i) and ii) the aqueous portion of the reaction mixture is removed and the reagents for the subsequent step are added in aqueous solution or water and the reagents are added separately.

2. The process of claim 1 wherein the water-soluble iron cyanide salt has formula $K_xFe(CN)_6$ wherein x is 3 or 4 and the water-soluble persulfate salt is selected from potassium persulfate and sodium persulfate.

3. The process of claim 1 wherein the base is KOH.

4. The process of claim 1 wherein the organic solvents are selected from toluene, ethylbenzene, and mixtures thereof.

5. The process of claim 1 wherein the substituted phenol is reacted with about 1 to about 5 molar equivalents of paraformaldehyde and about 2 to about 5 molar equivalents of concentrated aqueous hydrochloric acid.

6. The process of claim 1 wherein the substituted phenol is reacted with about 2 to about 3 molar equivalents of paraformaldehyde and about 3 to about 4 molar equivalents of concentrated aqueous hydrochloric acid to form the substituted 4-chloromethylphenol.

7. The process of claim 1 wherein the substituted 4-chloromethylphenol is reacted with about 1 to about 3 molar equivalents of a cyanide salt of formula MCN where M is K or Na and about 1 to about 5 mole percent of a catalyst of formula $R_4N^+X^-$ where R is $C_1$-$C_4$ alkyl and X is Cl or Br.

8. The process of claim 1 wherein the substituted 4-chloromethylphenol is reacted with about 1 molar equivalent of sodium cyanide and about 1 mole percent of tetrabutylammonium bromide to form the substituted 4-cyanomethylphenol.

9. The process of claim 1 wherein the substituted 4-cyanomethylphenol is reacted with about 0.1 to 1 equivalents of the water-soluble iron cyanide salt, about 0.1 to 1.0 equivalents of the water-soluble persulfate salt and about 1 to 3 equivalents of base.

10. The process of claim 1 wherein the substituted 4-cyanomethylphenol is reacted with less than about 0.25 equivalents of potassium hexacyanoferrate, about 1.0 equivalents of potassium persulfate and about 2.2 equivalents of KOH to form the substituted 7-cyano quinone methide.

11. The process of claim 1 wherein $R_1$ and $R_2$ are independently selected from $C_4$-$C_8$ alkyl.

12. The process of claim 9 wherein $R_1$ and $R_2$ are tert-butyl.

13. The method of claim 1 wherein the method is a one-pot synthesis, said one-pot synthesis characterized by steps i and ii being performed in the presence of a water solvent and an organic solvent and after each of steps i and ii the water portion of the reaction product is removed and the organic portion of the reaction product is used as is for subsequent steps without isolation of intermediate products.

* * * * *